United States Patent
Shimoni et al.

(10) Patent No.: US 7,488,486 B2
(45) Date of Patent: Feb. 10, 2009

(54) PHARMACEUTICAL COMPOSITIONS AND ARTICLES OF MANUFACTURE USEFUL IN REVERSAL OF A CLINICAL EPIOSODE OF AN INCURABLE DISEASE AND METHODS OF USE THEREOF

(75) Inventors: Zvi Shimoni, Netanya (IL); Mark Jonathan Niven, Bnei Brak (IL); Shlomo Bulvik, Kfar Haroeh (IL)

(73) Assignee: Sanz Medical Center-Laniado Hospital, Netanya (IL)

( * ) Notice: Subject to any disclaimer, the term of this patent is extended or adjusted under 35 U.S.C. 154(b) by 66 days.

(21) Appl. No.: 11/438,069

(22) Filed: May 22, 2006

(65) Prior Publication Data
US 2006/0210574 A1 Sep. 21, 2006

Related U.S. Application Data

(62) Division of application No. 10/414,011, filed on Apr. 16, 2003.

(60) Provisional application No. 60/377,953, filed on May 7, 2002.

(51) Int. Cl.
- *A61K 39/00* (2006.01)
- *A61K 39/12* (2006.01)
- *A61K 39/193* (2006.01)

(52) U.S. Cl. .............. 424/218.1; 424/204.1; 424/142.1; 424/134.1

(58) Field of Classification Search ........................ None
See application file for complete search history.

(56) References Cited

U.S. PATENT DOCUMENTS 4,665,159 A * 5/1987 Dobkin .................... 530/389.4

OTHER PUBLICATIONS

Shimoni et al., Treatment of West Nile Virus Encephalitis with Intravenous Immunoglobulin, Emerging Infectious Diseases, Letters, Jul. 2001, vol. 7, No. 4, p. 759.*

Omr-IgG-am, US Department of Health & Human Servoces Grants Orphan Drug Designation of Immune Globulin (Human) containing high titers of West Nile Virus antibodies for the treatment of the West Nile Virus infection Omr-IgG-am tm.*

Roehrig et al., Antibody Prophylaxis and Therapy for Flavivirus Encephalitis Infections, Annals New York Academy Of Sciences, 2001, vol. 951, pp. 286-297.*

Dalai et al., Prophylactic and therapeutic effects of human immunoglobulin on the pathobiology of HSV-1 infection, latency, and reactivation in mice, Journal of NeuroVirology. Feb. 2002, vol. 8, pp. 35-44.*

Weinberger et al., West Nile Fever Outbreak, Israel, 2000: Epidemiologic Aspects, Emerging Infectious Diseases, Jul. 2001, vol. 7, No. 4, pp. 686-691.*

* cited by examiner

*Primary Examiner*—Bruce Campell
*Assistant Examiner*—Sharon Hurt
(74) *Attorney, Agent, or Firm*—Curatolo Sidoti Co., LPA

(57) ABSTRACT

A method of reversing a clinical episode of a disease which is generally considered incurable in a subject. The method includes providing an immune-globulin preparation containing a detectable titre of antibodies to the disease which is generally considered incurable and administering the immune-globulin preparation to the subject. Preferably, the immune globulin preparation is a pool of immune globulin fractions gathered from blood of donors living in an area where the disease is endemic. Further disclosed are pharmaceutical compositions and articles of manufacture suited for use in practice of the method.

12 Claims, 1 Drawing Sheet

Figure 1    20
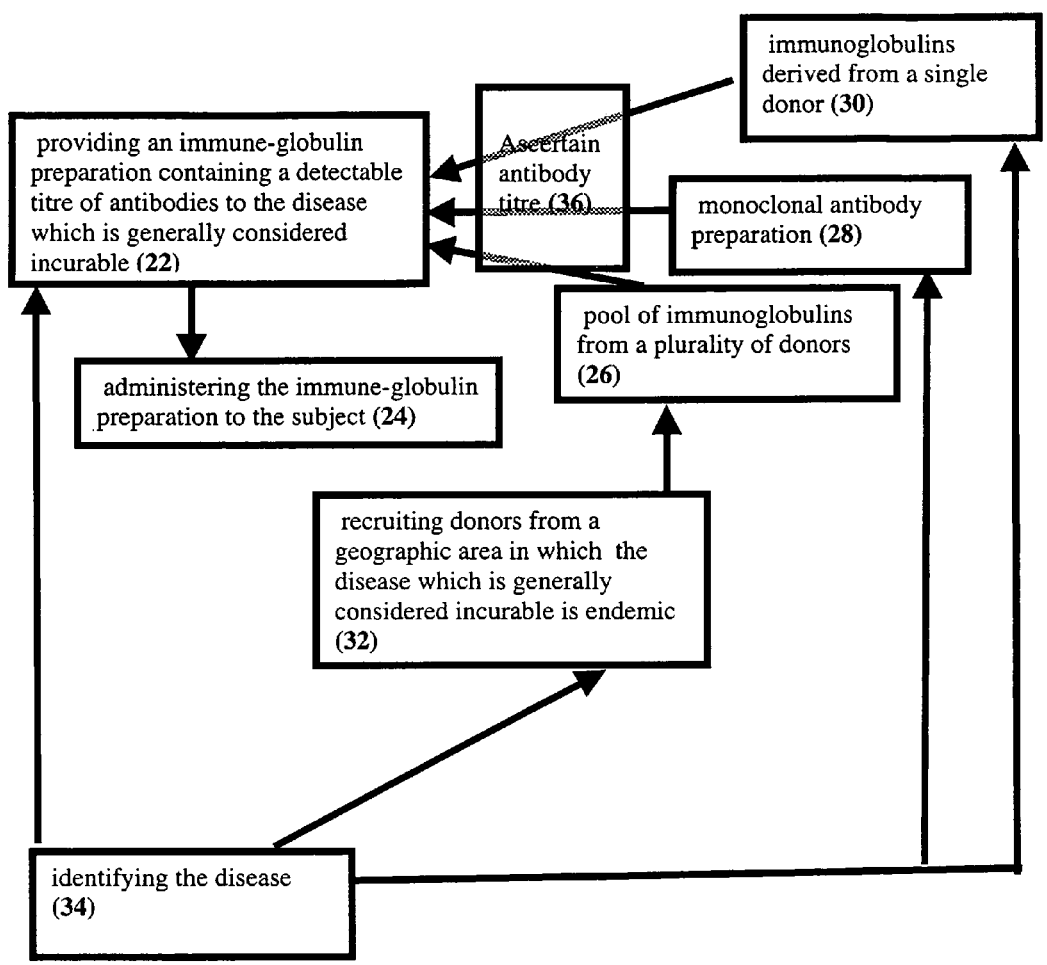

PHARMACEUTICAL COMPOSITIONS AND ARTICLES OF MANUFACTURE USEFUL IN REVERSAL OF A CLINICAL EPIOSODE OF AN INCURABLE DISEASE AND METHODS OF USE THEREOF

CROSS REFERENCE TO RELATED APPLICATIONS

This application is a divisional application of U.S. application Ser. No. 10/414,011 filed Apr. 16, 2003 which claims priority from U.S. patent application Ser. No. 60/377,953 filed on May 7, 2002. The aforementioned applications are incorporated by reference in the present application in their entirety

FIELD AND BACKGROUND OF THE INVENTION

The present invention relates to pharmaceutical compositions and articles of manufacture useful in reversal of a clinical episode of an incurable disease and to methods of use thereof. More particularly, the present invention relates to use of passive immunization with an immune-globulin preparation as a mode of treatment for an acute attack of a disease. The present invention has demonstrable clinical efficacy in treatment of West Nile Virus and is expected to demonstrate similar utility in a wide variety of maladies which are generally considered incurable or irreversible.

The use of antibodies in medicine is well known. Antibodies may be employed to provide active immunity or passive immunity.

Active immunity is achieved by vaccination with a material that triggers an immune response in the vaccinated subject. The material is most often an antigen preparation, but may be an antigenic precursor or a nucleic acid sequence encoding an antigen(s). Active immunization often occurs naturally as a result of infection. Thus, a person that has suffered a clinical episode of chicken pox is unlikely to be re-infected with that the virus which caused their initial clinical episode. Administration of the material triggers the immune system of the subject to produce immune globulins which are specific to the antigen(s) in (or produced by) the administered material. All active immunization protocols have, as an inherent disadvantage, a strict requirement for an available source of antigen or antigenic precursor. Further, the antigen or antigenic precursor must typically be administered prior to presentation of clinical symptoms, preferably prior to infection.

Passive immunity is achieved via direct introduction of immune globulin molecules, or active portions thereof, into a subject. No immune response from the subject is required. Theoretically, passive immunization is possible for all diseases. In practice, use of passive immunization has been limited. This is because passive immunization typically requires purposeful preparation of immune globulins which is an inherent disadvantage. Further, passive immunization has most often been employed after exposure to a disease but prior to onset of clinical symptoms. The most well known examples of passive immunization is administration of anti-venom after a snake bite and use of immuno-globulins to prevent rabies infection in a person bitten by an animal at risk for rabies.

Banking of blood and blood components including fractions enriched in immunoglogulins is routinely carried out in many modern medical centers. Thus, there is no shortage of available immuno-globulins.

Despite the theoretical possibility of passive immunization, and despite the availability of immuno-globulins, many diseases are considered incurable or untreatable and result in morbidity and/or mortality of infected subjects. Because many of these diseases are fatal, it has always been assumed that the availability of immune globulins in the general population is low. Therefore, medical practitioners have failed to look in blood banks for available solutions which rely upon the well established principles of passive immunity. Further, because many of these diseases are transmissible via blood transfer, standard medical advice is to disqualify infected, or even exposed, individuals as blood donors. Thus, blood donors are typically required to answer a battery of questions designed to ascertain if they have ever been exposed to, for example, HIV, Lyme's disease, malaria or spongiform encephalopathy. Exposed individuals are typically disqualified as donors. This practice should, for all intents and purposes, ettectively eliminate immune globulin molecules with a specificity for antigens associated with infectious diseases from the blood supply.

There is thus a widely recognized need for, and it would be highly advantageous to have, pharmaceutical compositions and articles of manufacture useful in reversal of a clinical episode of an incurable disease and methods of use thereof.

SUMMARY OF THE INVENTION

According to a one aspect of the present invention there is provided a method of reversing a clinical episode of a disease which is generally considered incurable in a subject. The method includes: (a) providing an immune-globulin preparation containing a detectable titre of antibodies to the disease which is generally considered incurable and (b) administering the immune-globulin preparation to the subject.

According to another aspect of the present invention there is provided a pharmaceutical composition for reversing a clinical episode of a disease which is generally considered incurable in a subject. The pharmaceutical composition includes, as an active ingredient, a therapeutically effective amount of an immune-globulin preparation containing a detectable titre of antibodies to the disease which is generally considered incurable and a physiologically acceptable carrier and/or excipient.

According to yet another aspect of the present invention there is provided an article of manufacture which includes packaging material and a pharmaceutical composition identified for reversing a clinical episode of a disease which is generally considered incurable in a subject contained within the packaging material. The pharmaceutical composition includes, as an active ingredient, a therapeutically effective amount of an immune-globulin preparation containing a detectable titre of antibodies to the disease which is generally considered incurable and a pharmaceutically acceptable carrier.

According to yet another additional aspect of the invebtion the immune-globulin preparation containing a detectable titre of antibodies to the disease which is generally considered incurable is used to purify at least one antigen or epitope which is subsequently used as a vaccine.

According to further features in preferred embodiments of the invention described below, the immune globulin preparation is selected from the group consisting of a pool of immuno-globulins from a plurality of donors, a monoclonal antibody preparation and immuno-globulins derived from a single donor.

According to still further features in the described preferred embodiments the immune-globulin preparation includes at least one immuno-globulin selected from the group consisting of IgG, IgM, IgA, and IgY.

According to still further features in the described preferred embodiments the plurality of donors are recruited from a geographic area in which the disease which is generally considered incurable is endemic.

According to still further features in the described preferred embodiments the geographic area includes at least a portion of an area selected from the group consisting of the state of Israel and territories administered thereby.

According to still further features in the described preferred embodiments the disease which is generally considered incurable is a viral disease selected from the group consisting of West Nile Virus, Hepatitis A, Hepatitis B, Hepatitis C, HIV, RSV, CMV, HSV, ESV, VSV, Ebola virus and tick borne encephalitis.

According to still further features in the described preferred embodiments administering is performed via a route of administration selected from the group consisting of intravenously, intraperitoneally, subcutaneously, intramuscularly, orally, introcularly, intranasally, intraocularly, vaginally and rectally.

According to still further features in the described preferred embodiments donor(s) are selected from the group consisting of human beings and non-human animals.

According to still further features in the described preferred embodiments the subject is selected from the group consisting of human beings and non-human animals.

According to still further features in the described preferred embodiments the subject suffers from impaired immune function.

The present invention successfully addresses the shortcomings of the presently known configurations by providing means for reversing a clinical episode of a disease which is generally considered incurable in a subject

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawing:

FIG. 1 is a flow diagram illustrating sequence(s) of events associated with performance of a method according to the present invention.

DESCRIPTION OF THE PREFERRED EMBODIMENTS

The present invention is of pharmaceutical compositions and articles of manufacture useful in reversal of a clinical episode of an incurable disease and to methods of use thereof. The present invention can be used to provide relief from clinical symptoms of an incurable disease by means of passive immunization with an immune-globulin preparation. The present invention has demonstrable clinical efficacy in treatment of West Nile Virus and is expected to demonstrate similar utility in a wide variety of maladies which are generally considered incurable or irreversible. Specifically, the present invention can be used to treat encephalitis.

The present invention is embodied by a method 20 of reversing a clinical episode of a disease which is generally considered incurable in a subject. The phrase "generally considered incurable" as used in this specification and the accompanying claims refers to those diseases to which medical science was unable to offer a clinically efficacious solution prior to the present invention (Keller and Stiehm (2000) Clin. Microbiol. Rev. 13(4): 602-614). As such, "generally considered incurable" includes, but is not limited to West Nile Virus, Hepatitis A, Hepatitis B, Hepatitis C, HIV, RSV, CMV, HSV, ESV, VSV, Ebola virus and tick borne encephalitis. Bacterial diseases which are not amenable to treatment are further included in the definition of "generally considered incurable" as are prion mediated diseases (e.g. Creutzfeldt-Jacobsen disease and BSE).

Method 20 includes providing 22 an immune-globulin preparation containing a detectable titre of antibodies to the disease which is generally considered incurable. Preferably, providing 22 is facilitated by identifying 34 the disease. The immune globulin preparation may be, for example, a pool of immuno-globulins 26 from a plurality of donors, a monoclonal antibody preparation 28, an immuno-globulin preparation derived from a single donor 30 or a combination thereof.

If immuno-globulins 26 from a plurality of donors are employed, the donors are preferably recruited 32 from a geographic area in which the disease which is generally considered incurable is endemic. Preferably, definition of a geographic area is facilitated by identifying 34 the disease. The example presented hereinbelow serves to establish that, with respect to West Nile Virus, the state of Israel and territories administered thereby, or a portion thereof, may serve as a geographic area to which the disease is endemic.

If immuno-globulins 30 from a single donor are employed, the donor may be a donor that has been specially prepared. Preferably, preparation of a donor is contingent upon identifying 34 the disease. Special preparations might include, but are not limited to, vaccination with the disease which is generally considered incurable or an antigen preparation derived therefrom. Alternately or additionally the single donor may be chosen because they are known to have been exposed, or have been at high risk for exposure. Such individual donors might include hospital personnel working closely with infected individuals, spouses of infected individuals and children born to infected mothers.

Providing 22 an immune-globulin preparation refers to providing at immuno-globulins such as, for example, IgG, IgM, IgA, and IgY, active portions thereof and/or combinations thereof.

Method 20 further includes administering 24 the immune-globulin preparation to the subject. Administration may be via a route of administration such as, for example, intravenous, intraperitoneal, subcutaneous, intramuscular, oral, intraocular, intranasal, intraocular, vaginal or rectal.

Method 20 is preferably practiced by employing a pharmaceutical composition. The pharmaceutical composition includes, as an active ingredient, a therapeutically effective amount of an immune-globulin preparation as described hereinabove and a physiologically acceptable carrier and/or excipient.

The pharmaceutical composition is preferably incorporated into an article of manufacture which includes packaging material and a pharmaceutical composition identified for reversing a clinical episode of a disease which is generally considered incurable in a subject contained within the packaging material. The pharmaceutical composition is as described hereinabove For purposes of this specification and the accompanying claims, the term "donor" refers to any human being or non-human animal which produces immune globulins. The term further includes cell cultures and/or plants which have been manipulated using molecular biological techniques so that they produce immune globulins, although they would not naturally do so. Similarly, the subject may be either a human being or a non-human animal.

As detailed in an example hereinbelow, method 20 preferably involves administration of intravenous immuno-globulin containing high titers of antibodies to West Nile virus. It is therefore understood that ascertaining antibody titre 36 is preferably part of method 20. Method 20 preferably further involves the intravenous administration 24 of an immuno-globulin preparation prepared from pooled 26 immuno-globulins from donors from a region 32 in which West Nile virus is endemic, such as Israel.

Thus, according to one preferred embodiment of the invention, method 20 relies upon administration 24 of intravenous immuno-globulin prepared from pooled immuno-globulins 26 from donors in Israel 32. One skilled in the art of medicine will be able to determine parameters for administration 24. The dosage and dosage schedules presented in the example are those that are standard in the art for use of intravenous immuno-globulin in treatment of disorders such as, for example, idiopathic thrombocytopenic purpura, or severe bacterial disease such as invasive streptococcal disease, particularly in immuno-compromised individuals.

West Nile virus is endemic in Israel. The overwhelming majority of infections are mild and asymptomatic, but there have been periodic symptomatic outbreaks (Cohen et al. (1999) Public Health Rev 27:217-30). In August 2000, an epidemic of West Nile virus broke out in Israel, with more than 260 confirmed cases and 20 deaths by the end of September 2000. At that time, the only treatment for west Nile Virus was supportive. No specific in vivo therapy had demonstrable clinical efficacy, although ribavirin had shown promise in in vitro studies (Jordan et al. (2000) J Infect Dis. 182: 1214-17.).

The reservoir for West Nile Virus is birds, specifically commercial poultry flocks. It is well known that egg yolks contain high concentrations of immuno-globulins, primarily IgY. The specific immuno-globulins deposited in the egg are a reflection of the disease history of the female bird laying the eggs. Thus, according to one embodiment of method 20 recruiting donors 32 might involve identification of a poultry flock which has been exposed to West Nile Virus. Alternately, or additionally a single donor 30 might be a laying hen producing eggs over a period of time.

Alternately or additionally, donor 30 may be a cell culture or a mouse producing monoclonal antibodies, preferably humanized monoclonal antibodies.

The present invention is expected to find especial utility in subjects which suffer from impaired immune function. This impairment of immune function may be the result of, for example, a genetic disorder, a disease (e.g. HIV), or use of immunosuppressive drugs. Immunosuppressive drugs may be employed, for example, to prevent transplant rejection or to alleviate symptoms of an autoimmune disorder (e.g. lupis).

The immune globulin preparation employed in the present invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the immuno-globulins accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum Arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane. trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical compositions described herein are preferably formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (immuno-globulin) effective to alleviate or ameliorate symptoms of a disorder (e.g., West Nile Virus induced coma) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in other animals or humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress angiogenesis (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device. such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The terms "immune globulin" and "immunoglogulin" as used in this specification and the accompanying claims refer to compositions which contain one or more antigen or epitope binding molecules which are also referred to in the literature collectively as "antibody".

The term "antibody" as used in this invention includes intact molecules as well as functional fragments thereof, such as Fab, F(ab')2, and Fv that are capable of binding to macrophages. These functional antibody fragments are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab')2 is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypepticle linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

As used in this invention, the term "epitope" means any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single potypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

Humanized forms of non-human (e.g., murine) antibodies are chimeric molecules of immuno-globulins, immuno-globulin chains or fragments thereof (such as Fv, Fab, Fab', F(ab').sub.2 or other antigen-binding subsequences of antibodies) which contain minimal sequence derived from non-human immuno-globulin. Humanized antibodies include human immuno-globulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immuno-globulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immuno-globulin and all or substantially all of the FR regions are those of a human immuno-globulin consensus sequence. The humanized antibody optimally also will comprise at least a portion of an immuno-globulin constant region (Fc), typically that of a human immuno-globulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR seqences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss. p. 77 (1985) and Boerner et al., J. Immunol., 147(1):86-95 (1991)]. Similarly, human antibodies can be made by introducing of human immuno-globulin loci into transgenic animals, e.g., mice in which the endogenous immuno-globulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996): Neuberger, Nature Biotechnology 14, 826 (1996); Lonberg and Huszar, Intern. Rev. Immunol. 13 65-93 (1995).

EXAMPLES

It is to be understood that the invention is not limited in its application to the details set forth in the following examples. The invention is capable of other embodiments or of being practiced or carried out in various ways. Also, it is to be understood that the phraseology and terminology employed herein is for the purpose of description and should not be regarded as limiting.

Additional objects, advantages, and novel features of the present invention will become apparent to one ordinarily skilled in the art upon examination of the following example, which is not intended to be limiting. Additionally, each of the various embodiments and aspects of the present invention finds experimental support in the following examples.

Example 1

Administration of an Immune-globulin Preparation Reverses Advanced West Nile Virus Encephalitis An apparent dramatic response to intravenous immunoglobulin in an immunosuppressed patient suffering from advanced West Nile Virus induced encephalitis was observed (Shimoni et al. (2001) Emerging Infectious Diseases 7 (4): 759) in a clinical setting.

Briefly, a 70-year-old woman was admitted to the hospital because of fever and vomiting of 24 hours' duration. The subject had a 12-year history of chronic lymphatic leukemia (Rai stage II) but was not on treatment. A routine outpatient assessment 1 week earlier had shown no unexpected findings.

On physical examination the subject appeared generally well, with temperature 39.0° C., regular pulse 100/minute, and blood pressure 130/70. Apart from splenomegaly 2-3 cm below the costal margin, there were no abnormal physical signs, including lymphadenopathy. Chest X ray results were normal. Hb was 12 g/dL. HCt 32%. mean corpuscular volume 84, leukocyte count $280\times10^9$/L (90% lymphocytes, 13% neutrophils, and 10% monocytes), platelet $280\times10^9$/L, Coombs negative. Subject's biochemical profile was entirely within the normal range. Blood and urine cultures were negative. Immuno-globulin G (IgG) was 14.5 g/L, IgM 2.6 g/L, and IgA 2.6 g/L.

Forty-eight hours after admission, dysarthria with episodes of impaired consciousness developed. After a further 24 hours, the subject was in deep coma (Glasgow Coma Scale, 6). Empiric treatment for presumed central nervous system infection was begun with ceftriaxone, ampicillin, acyclovir, and amphotericin B. Results of cranial computerized tomography were normal. A lumbar puncture was performed and showed clear cerebrospinal fluid (CSF) at normal pressure. CSF protein was 1.04 g/L, glucose 2.4 mmol/L, and leukocyte count 162/$mm^3$ (90% mononuclear cells). Gram stain was negative, as were bacterial culture, cryptococcal antigen, and results of a polymerase chain reaction test for herpes viruses. IgM antibodies against West Nile virus were positive in both serum and CSF.

With the definite diagnosis of West Nile encephalitis, all antimicrobial treatment was stopped. Because of the chronic lymphatic leukemia and presumed immunosuppression, administration of intravenous immuno-globulin (Omr-IgG-am, Omrix Biopharmaceutical Ltd, Tel Hashomer, Israel), 0.4 g/kg was undertaken. This dosage was based upon published recommendations for preventive immunization in patients with a similar medical history (Cooperative Group for the Study of Immuno-globulin in Chronic Lymphocytic Leukemia. (1988) N Engl J Med 1319:902-7). The subject's neurologic condition remained unchanged (Glasgow coma scale, 5-6) for the next 2 days but then began to improve. Over the subsequent 5 days, subject's level of consciousness returned to normal.

This unexpected result indicates that treatment with immune globulins can reverse clinical symptoms of a disease, even a disease which is generally considered incurable.

Example 2

Characterization of Immune-globulin Preparation

In order to ascertain the reason for the dramatic response described in example 1, several batches of pooled immunoglobulin from different sources for were screened for antibodies to West Nile virus.

Intravenous immuno-globulin preparations from donors in Israel, such as the one employed in example 1, contained high titers (1:1600) of such antibodies.

Similar immuno-globulin preparations from the USA had no detectable antibody. The measurements of West Nile virus antibody were performed in the Central Virology Laboratory, Ministry of Health of Israel. These results indicate that the startling success reported in example 1 was a direct result of West Nile Virus antibodies in the administered material.

Therefore any immuno-globulin preparation which contains sufficient amounts of specific antibodies to a pathogen causing clinical symptoms in a subject should be capable of alleviating those symptoms.

Example 3

Administration of an Immune-globulin Preparation Reverses Advanced West Nile Virus Encephalitis Following the surprising clinical outcome described in example 1, the inventors employed similar method in an additional case. The outcome was similar to that reported in example 1 (Hamdan et al. (2002) Transpl. Infect. Dis. 4(3): 160-162.)

Briefly, a 42 year old male patient with confirmed West Nile Virus encephalitis and deteriorating level of consciousness was treated as described hereinabove in example 1 with the same immune globulin preparation described in example 2. The subject had previously undergone lung transplant surgery and was in an immuno-suppressed state in order to prevent transplant rejection.

Following treatment the patient improved rapidly of 24 hours and continued to improve so that no sign or symptom of encephalitis remained after 48 hours.

This result confirms that indicates that treatment with immune globulins can reverse clinical symptoms of a disease, even a disease which is generally considered incurable.

Although the invention has been described in conjunction with specific embodiments thereof it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of reversing a clinical episode of West Nile Virus in a clinically ill individual, the method comprising:
   (a) providing a therapeutically effective amount of an immune-globulin preparation prepared from a pool of immuno-globulins from a plurality of donors and containing a detectable titer of antibodies to West Nile Virus,
   (b) administering said immune-globulin preparation to the clinically ill individual after the West Nile Virus has entered the central nervous system.

2. The method of claim 1, wherein said immune-globulin preparation includes at least one immuno-globulin selected from the group consisting of IgG, IgM, IgA, and IgY.

3. The method of claim 1, further comprising recruiting said plurality of donors from a geographic area in which West Nile Virus is endemic.

4. The method of claim 3, wherein said geographic area includes at least a portion of an area selected from the group consisting of the state of Israel and territories administered thereby.

5. The method of claim 1, wherein said administering is performed via a route of administration selected from the group consisting of intravenously, intraperitoneally, subcutaneously, intramuscularly, orally, intraocularly, intranasally, vaginally and rectally.

6. The method of claim 1, wherein said preparation further comprises a component selected from the group consisting of a physiologically acceptable carrier and/or an excipient.

7. A method of treatment of West Nile Virus infections in humans, the method comprising administering to a human infected with West Nile Virus, after the West Nile Virus has entered the central nervous system, a pharmaceutical composition comprising, as an active ingredient, a therapeutically effective amount of an immune-globulin preparation prepared from a pool of immuno-globulins from a plurality of donors and containing a detectable titer of antibodies to West Nile Virus and a pharmaceutically acceptable carrier.

8. The method of claim 7, wherein said immune-globulin preparation comprises at least one immuno-globulin selected from the group consisting of IgG, IgM, IgA, and IgY.

9. The method of claim 7, wherein said immune globulin preparation is prepared from a pool of immuno-globulins from a plurality of donors.

10. The method of claim 7, further comprising recruiting said plurality of donors from a geographic area in which West Nile Virus is endemic.

11. The method of claim 10, wherein said geographic area includes at least a portion of an area selected from the group consisting of the state of Israel and territories administered thereby.

12. The method of claim 7, wherein said administering is performed via a route of administration selected from the group consisting of intravenously, intraperitoneally, subcutaneously, intramuscularly, orally, intraocularly, intranasally, vaginally and rectally.

* * * * *